United States Patent [19]

Soodak et al.

[11] 4,047,820

[45] Sept. 13, 1977

[54] CONSTANT TEMPERATURE, MULTIPLE SAMPLE, ROTARY CHANGER

[75] Inventors: Charles Soodak, Silver Spring; David L. Lessner, Baltimore; James H. Macemon, Glen Burnie, all of Md.

[73] Assignee: Baxter Travenol Laboratories, Inc., Deerfield, Ill.

[21] Appl. No.: 687,883

[22] Filed: May 19, 1976

[51] Int. Cl.$^2$ .................................. G01N 21/16
[52] U.S. Cl. ................................. 356/244; 250/576
[58] Field of Search .................... 356/244, 96, 97; 250/576

[56] References Cited

U.S. PATENT DOCUMENTS

| | | | |
|---|---|---|---|
| 3,551,062 | 12/1970 | Brown | 356/244 |
| 3,806,259 | 4/1974 | Boostrom et al. | 356/244 |

*Primary Examiner*—Vincent P. McGraw
*Attorney, Agent, or Firm*—Henry W. Collins; Paul C. Flattery; Richard G. Kinney

[57] ABSTRACT

A rotary sample changer for a spectrofluorometer has a revolving turret base which can be indexed and which carries an interchangeable sample carrier. Different sample carriers accommodate test cells, test tubes and cuvettes of different sizes and shapes.

The revolving turret base and the interchangeable rotary sample carriers are constructed of material having good thermal conductivity and rotate on a large stationary hollow axle which is thermostated by thermally controlled internal fluid circulation to act as a heat source or sink to the samples. Thus, the sample carriers can readily be interchanged without disturbing the plumbing by which the thermostatic fluid is circulated.

The revolving turret base is detented at the stations to which it is indexed without kinematic ambiguity and without application of any cocking force. Two spring biased ball detents, symmetrically spaced 180° about the axis of rotation, are provided. At the four index stations one ball catches on one of two indexing grooves spaced 90° apart, while the other ball bears against a flat.

10 Claims, 2 Drawing Figures

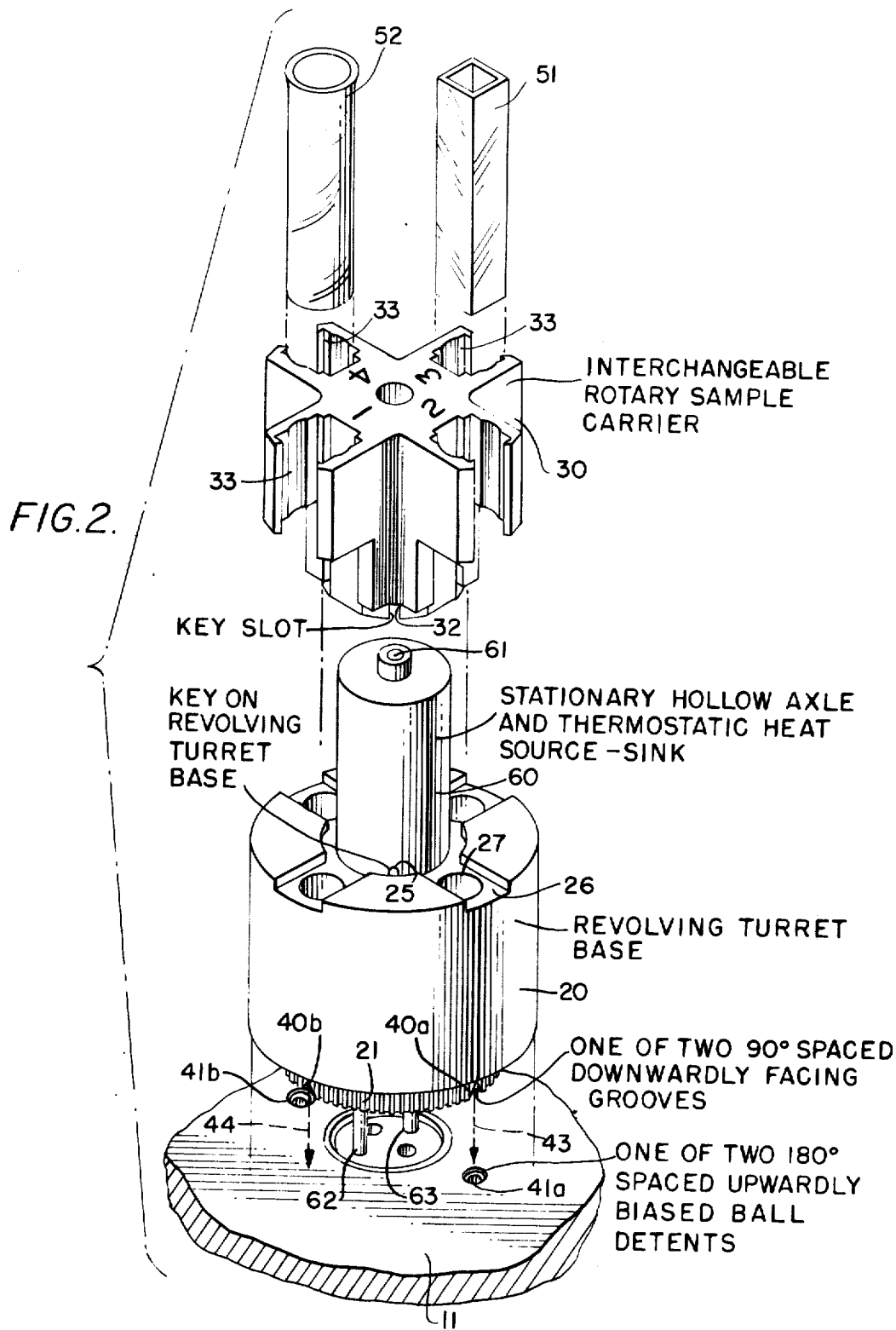

CONSTANT TEMPERATURE, MULTIPLE SAMPLE, ROTARY CHANGER

CROSS REFERENCE TO RELATED APPLICATIONS

The sample changer disclosed herein is of general utility. It is part of a newly developed spectrofluorometer having other inventive features which are unrelated to the instant invention, except for use in the same commercial embodiment.

SUMMARY

In spectroflurometers and many other optical test instruments, it is desirable to have a sample changer which permits different samples to be brought successively to an optical testing point. The sample changer should accommodate samples in the different kinds of containers which are used to hold samples. Included are test tubes, parallel-sided test cells and cuvettes.

A sample changer can accept different containers by using, as its sample support portion, interchangeable sample carriers, each specifically designed to accept the shape and size of particular sample containers.

The sample carrier should be thermostated to keep the samples at a proper temperature. In the past this has been accomplished by flowing termally controlled fluid through passages in the sample carrier. Such an expedient requires the thermostatic fluid plumbing system to be disconnected and reconnected when changing the sample carrier.

In accordance with the invention, the thermally controlled fluid system for a sample changer is located in a part of the sample changer which is not interchanged, and acts as a heat source or sink to the samples by thermal conduction through the interchangeable part which supports the samples. Thus, when changing sample carriers, it is not necessary, as it was in the past, to disconnect and reconnect the thermal fluid plumbing system.

VIEWS OF DRAWING

FIG. 2 is an exploded perspective view of a portion of the sample changer.

DETAILED DESCRIPTION

Figure 1:
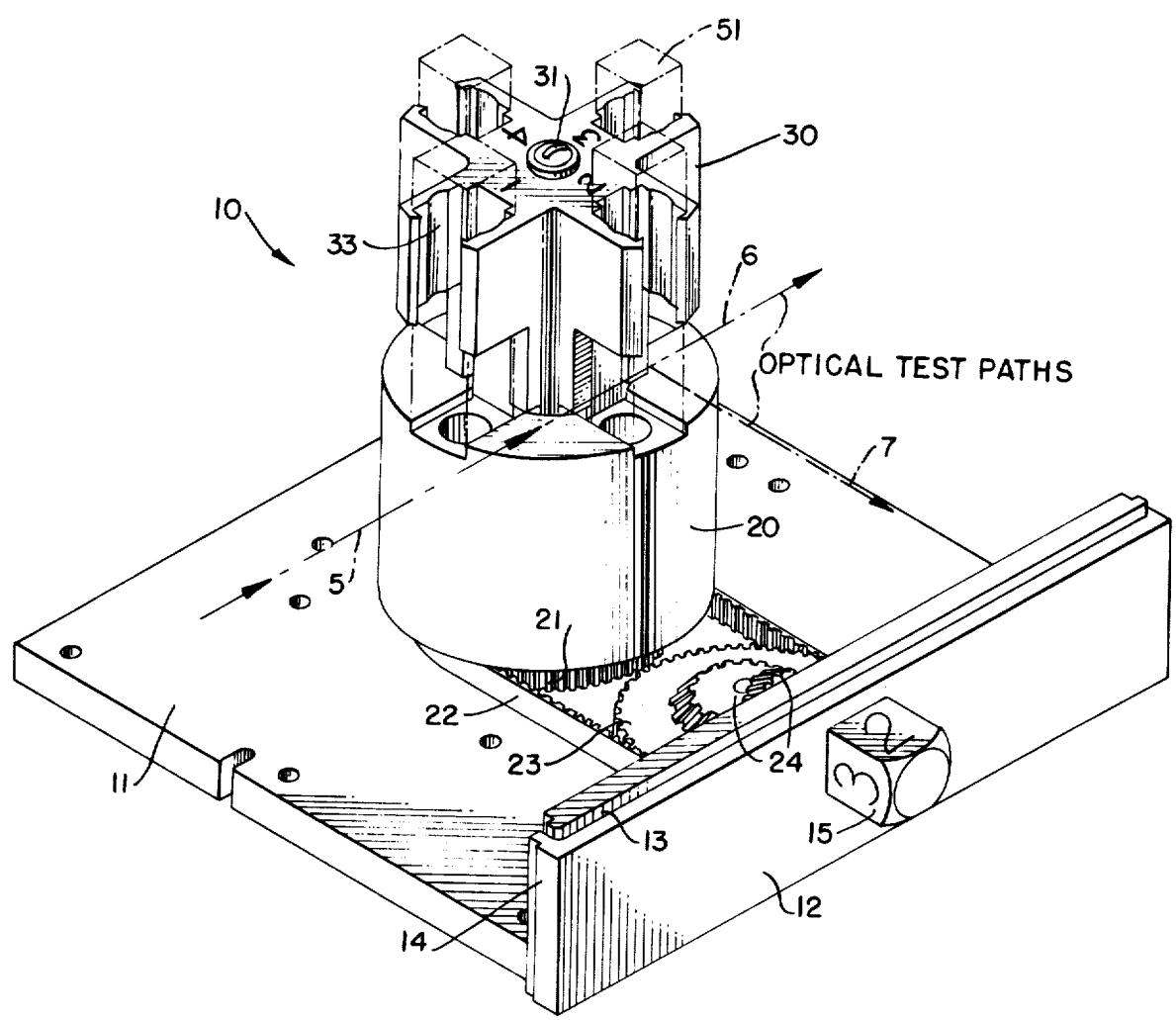
FIG. 1 is a perspective view of the sample changer.

In FIG. 1 the sample changer is seen as a complete assembly, ready for loading with sample cells. The positions which four parallel sided sample cells 51 would occupy are shown in phantom lines.

An entrance ray 5 of light, which may be monochromatic and may be in the ultraviolet range, is shown as going into and through the location of one of the parallel sided sample cells 51 and emerging as a direct exit ray 6. The entrance ray 5 may also produce scatter rays in various directions lying at different angles to the entrance ray 5; one of these scatter rays is represented by ray 7. Furthermore, the entrance ray 5 may excite fluorescent radiation in the sample, over a wide range of angles, and one of the emitted fluorescent rays is also represented by ray 7.

A measurement of the intensity of the direct exit ray 6 or the intensity of the scatter emission of fluorescent emission ray 7 provides part of the information needed to determine the optical properties of the sample. These properties are of interest, among other things, in the study and diagnosis of medical conditions.

The sample changer 10 is built on a base 11 to which front panel 12 is attached. Because the optical tests are made at extremely low light levels, it is necessary to make the tests in the dark. Accordingly, the front panel is provided with light-trap lips 13 and 14, which cooperate with a cover and with other parts of the equipment, not shown, to keep room light away from the samples. The front panel is provided with a knob 15, for indexing the revolving turrent base 20 and the interchangeable rotary sample carrier 30 so as to sequentially bring the four samples up to the entrance ray 5. The particular sample on which the entrance ray 5 impinges is indicated by the numerals on each of the faces of knob 15. The locations 1 to 4 of the interchangeable rotary sample 30 carrier can be correspondingly labeled. Knob 15 rotates the revolving turret base 20 through means which includes miter gears 24, driving gear 23, drive belt 22 and driven gear 21, the last being fixed to the revolving turret base 20.

The revolving turret base 20 rotates on a large stationary hollow axle 60, which is seen in the partially exploded view of FIG. 2. In that view the interchangeable rotary sample carrier 30 has been raised up, off the stationary hollow axle 60 and the revolving turret base 20, while the revolving turret base 20 is shown in correct operating relationship with the stationary hollow axle 60. However, the stationary hollow axle 60 is shown as being raised up, off the base 11, so as to expose to view the inlet and outlet nipples 62 and 63. These nipples provide circulating temperature-controlled water to the interior of the stationary hollow axle 60, for the purpose which will be explained below.

When stationary hollow axle 60 is lowered downwardly a distance indicated by dotted lines 43 and 44, the stationary hollow axle 60 will seat properly on base 11 and the driven gear 21 of turret base 20 will just clear the base 11.

The particular interchangeable rotary sample carrier 30 which is depicted in FIG. 2 is adapted to accept either round test tubes 52 or parallel sided test cells 51. It will be seen that the pockets or clips or receivers 33 for receiving these sample carriers are broached with intersecting square and round cross sections. When a round cross section test tube 52 is in the receiver 33 of interchangeable rotary sample carrier 30, assembled on revolving turret base 20, as shown in FIG. 1, the rounded bottom of the test tube sits in and is supported by the edge of aperture 27 of the revolving turret base, while if a parallel sided test cell 51 of square cross section is seated in place in receiver 33, its bottom end sits on flat supporting surface 26.

The interchangeable rotary sample carrier 30, when assembled on stationary hollow axle 60 and revolving turret base 20, is keyed to the latter in an unambiguous angular orientation by means of key 25 and key slot 32.

The interchangeable rotary sample carrier 30 is made of material having high thermal conductivity. Thus, the samples accept or reject heat, by way of thermal conduction through the interchangeable rotary sample carrier 30 to the stationary hollow axle 60, which acts respectively as a heat source or heat sink for the samples. Thus, the samples are thermostated to the temperature of the temperature-controlled water which circulates in stationary hollow axle 60.

While only one particular form of interchangeable rotary sample carrier 30 has been illustrated, other forms, adapted to the shape of other sample containers, can be substituted. This requires merely the removal of screw 31 from screw hole 61, and does not require the disassembly of the circulating water system plumbing. Thus, a change of sample carrier is simple and requires little time.

Since the samples must be indexed, an indexing detent is provided. In the invention the detenting is performed at the turret, rather than at knob 15. The bottom side of driven gear 21 is provided with two downwardly facing radial grooves 40a and 40b, which are spaced at right angles. That is, there are downwardly facing grooves at, say, zero and 90° orientation, with no grooves at 180° and 270° orientation. The two downwardly facing grooves cooperate, one at a time, with two upwardly facing ball detents 41a and 41b, which are spaced 180° apart, and which are spring biased upwardly. While one ball detent pushes upwardly against one of the downwardly facing grooves in the driven gear 21 (and thereby detents the turret) the other ball detent pushes upwardly against the flat underside of the driven gear 21.

It will be seen from FIG. 2, that when the driven gear 21 is lowered to its operating position, the downwardly facing groove 40a lowers according to the dotted line 43 to meet ball detent 41a. However, downwardly facing groove 40b lowers according to dotted line 44 to lie over a vacant portion of base 11.

Since the upward pushes of the two ball detents are about equal in force, but on directly opposite sides of stationary hollow axle 60, it follows that the ball detents do not tend to cock or jam the sample changer. Furthermore, since only one ball-groove action occurs at a time, the detenting action is without angular ambiguity, such as could occur with two 180° spaced ball detents and four 90° spaced grooves.

It will be evident, with this system of indexing, that the spring biased ball detents should always be spaced equally about the axis of rotation, at 180° for two, 120° for three, etc., so as to provide a balanced non-cocking detenting force. Furthermore, the product of the number of balls detent and the number of grooves gives the number of indexing positions. For nine equally spaced indexing positions, three ball detents spaced 120° are used with three grooves. The grooves can be arranged in many ways, of which two are:

0° — 40° — 80°
0° — 80° — 160°

Although, for purposes of exposition, the two downwardly facing grooves 40a and 40b are shown as coming through the teeth of driven gear 21, it is to be understood that, as in a prototype embodiment, the grooves need extend radially a distance only long enough to span the radial location of the upwardly biased ball detents 41a and 41b.

Various other variations will be obvious to a person skilled in the art.

We claim:

1. In a constant temperature sample changer for multiple samples contained in sample containers:
a hollow stationary axle;
a revolving turret base mounted on said stationary hollow axle for rotation thereon;
means to index said revolving turret base to any of a sequence of angular orientations;
a readily removable interchangeable sample carrier mounted on said stationary hollow axle for rotation thereon adjacent said turret base;
means to unambiguously key said interchangeable sample carrier to said revolving turret base, whereby, when said revolving turret base is indexed, said interchangeable rotary sample carrier is correspondingly indexed;
said interchangeable sample carrier having receivers of shape adapted to receive said sample containers, said receivers being located angularly about said interchangeable sample carrier at positions correspondingly to said sequence of angular orientations;
said interchangeable sample carrier and said stationary hollow axle being made of a material having high heat conductivity;
means to maintain said stationary hollow axle at a constant temperature, whereby, by means of heat conduction, said containers of samples are thermostated to the temperature of said stationary hollow axle.

2. The subject matter of claim 1 wherein
the means to maintain said stationary hollow axle at a constant temperature includes means for flowing liquid through the hollow of said stationary axle.

3. The subject matter of claim 1 having:
spring biased detenting means for detenting said revolving turret base at each of said sequence of angular orientations.

4. The subject matter of claim 1 having:
a front panel control means for setting said revolving turret base to any selected one of said sequence of angular orientations.

5. The subject matter of claim 4 in which
said front panel control includes a rotary knob, adapted for selective rotation by hand;
and indicia, cooperatively associated with said knob, to indicate that one of said sequence of angular orientations has been selected.

6. In a constant temperature sample changer for multiple samples contained in sample containers:
a hollow stationary axle;
a revolving turret base mounted on such stationary hollow axle for rotation thereon;
means to index said revolving turret base to any of a sequence of angular orientations;
a readily removable interchangeable sample carrier mounted on said stationary hollow axle for rotation thereon adjacent said turret base;
means to unambiguously key said interchangeable sample carrier to said revolving turret base, whereby, when said revolving turret base is indexed, said interchangeable rotary sample carrier is correspondingly indexed;
said interchangeable sample carrier having receivers of shape adapted to receive said sample containers, said receivers being located angularly about said interchangeable sample carrier at positions corresponding to said sequence of angular orientations;
said indexing means including at least two spring biased ball detents, evenly angularly distributed about the axis of rotation of said revolving turret base;
said indexing means further including a flat member having grooves radial to said axis of rotation;
said spring biased ball detents and said flat member being arranged in confronting relationship so that said spring biased balls detents bear against said flat member and slide thereon as said flat member is rotated relative said spring biased ball detents;

said grooves being so arranged that only one spring biased ball detent can catch in a groove at a time, and only at a corresponding one of said sequence of angular orientations.

7. The subject matter of claim 6 having:
a front panel control means for setting said revolving turret base to any selected one of said sequence of angular orientations.

8. The subject matter of claim 7 in which
said front panel control includes a rotary knob, adapted for selective rotation by hand;
and indicia, cooperatively associated with said knob, to indicate what one of said sequence of angular orientations has been selected.

9. The subject matter of claim 7 in which:
said interchangeable sample carrier and said stationary hollow axle are made of a material having high heat conductivity; and
having means to maintain said stationary hollow axle at a constant temperature, whereby, by means of heat conduction, said containers of samples are thermostated to the temperature of said stationary hollow axle.

10. The subject matter of claim 9 wherein
the means to maintain said stationary hollow axle at a constant temperature includes means for flowing liquid through the hollow of said stationary axle.

* * * * *